United States Patent [19]

Desecki et al.

[11] 4,233,974
[45] Nov. 18, 1980

[54] SPINAL NEEDLE ASSEMBLY

[75] Inventors: Vince Desecki, Ingleside; Carl Filipowicz, Lindenhurst, both of Ill.

[73] Assignee: Baxter Travenol Laboratories, Inc., Deerfield, Ill.

[21] Appl. No.: 939,851

[22] Filed: Sep. 5, 1978

[51] Int. Cl.³ .............................................. A61M 5/00
[52] U.S. Cl. ...................................... 128/215; 128/221
[58] Field of Search ........................ 128/215, 221, 347

[56] References Cited
U.S. PATENT DOCUMENTS

| 1,757,680 | 5/1930 | Neil | 128/221 |
|---|---|---|---|
| 1,793,068 | 2/1931 | Dickinson | 128/221 |
| 2,559,474 | 7/1951 | Son | 128/215 |
| 2,755,801 | 7/1956 | Morando | 128/221 |
| 2,764,978 | 10/1956 | Everett | 128/215 |
| 2,952,256 | 9/1960 | Meader et al. | 128/221 |
| 3,329,146 | 7/1967 | Waldman, Jr. | 128/221 |

*Primary Examiner*—Henry K. Artis
*Attorney, Agent, or Firm*—Paul C. Flattery; John P. Kirby; George H. Gerstman

[57] ABSTRACT

A spinal needle assembly in which means are provided for bridging the end cap of the obturator and the hub of the cannula to prevent relative axial movement between the obturator and cannula.

5 Claims, 10 Drawing Figures

FIG. 1
FIG. 2
FIG. 2A
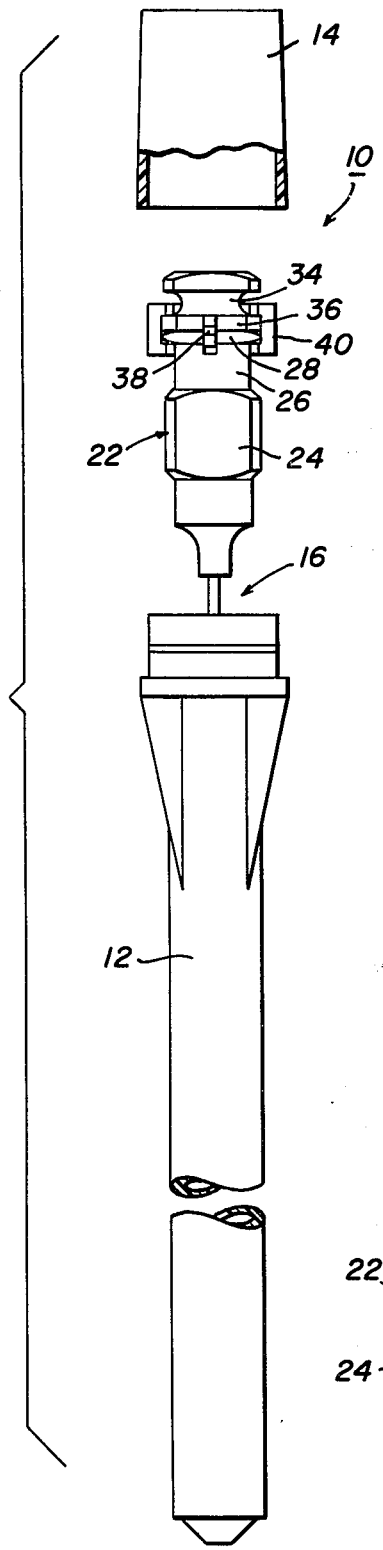
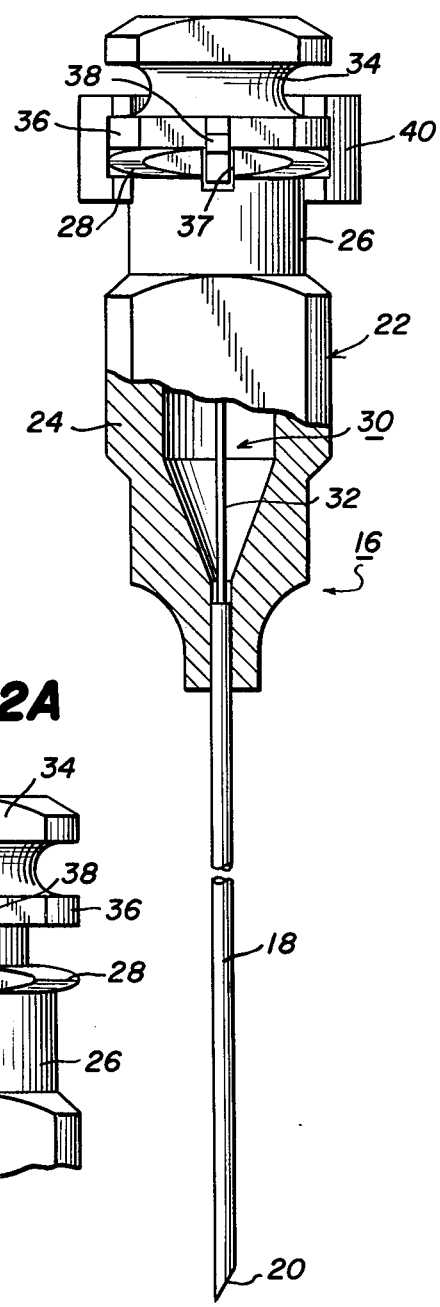
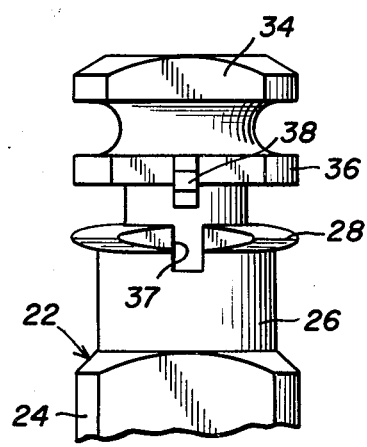

SPINAL NEEDLE ASSEMBLY

BACKGROUND OF THE INVENTION

This invention relates to a novel spinal needle assembly.

Typical spinal needle assemblies comprise an obturator having an end cap, a cannula having a needle bevel at one end and a hub at the opposite end, and a housing for the obturator and the cannula. The obturator extends into the cannula so that the end of the obturator opposite its end cap is substantially aligned with the bevel at the one end of the cannula, so as to prevent coring during insertion of the spinal needle.

Prior to or during insertion of the spinal needle, occasionally the obturator will become disengaged from the cannula. This problem is particularly serious with smaller diameter gauges, when the unit is inverted by the operator. Such disengagement or backoff of the obturator from the cannula is a serious problem and can create the environment for potential tissue traps which can later be deposited within the subarachnoid space, possibly resulting in the formation of epidermoid tumors.

Typically, the spinal needle assembly utilizes a cap dink, which serves to align the obturator cap with the cannula hub. However, it has been found that this cap dink does not necessarily maintain the cap and hub in proper aligned relationship, particularly when the spinal needle assembly is inverted or tilted drastically prior to insertion.

It is, therefore, an object of the present invention to provide means for maintaining the obturator within the lumen of its mated cannula. However, it is important that the operator have the ability to remove the obturator quickly and smoothly. Thus, any means for maintaining the obturator within the cannula must be easy to remove and must enable simple, smooth and rapid removal of the obturator with respect to the cannula.

Further, while the typical spinal needle assembly has utilized a hub slot and cap dink for aligning the cap and hub, the slot/dink relationship is designed as a bevel match locator, and is not intended to be an obturator locking device.

We have discovered a system by which the obturator and the cannula can be effectively locked in place and properly aligned during insertion, yet the obturator can be pulled rapidly and smoothly from the cannula once insertion has been effected.

It is, therefore, an object of the present invention to provide a spinal needle assembly having obturator backoff prevention means.

Another object of the present invention is to provide a spinal needle assembly in which the obturator can be removed quickly and smoothly.

Other objects and advantages of the present invention will become apparent as the description proceeds.

SUMMARY OF THE INVENTION

In accordance with the present invention, a spinal needle assembly is provided in which an obturator having an end cap extends into a cannula having a needle bevel at one end and a hub at the opposite end for engagement with the cap. The assembly further has means for aligning the obturator and the cannula.

The improvement comprises means for bridging the end cap and the hub to prevent relative axial movement between the obturator and the cannula. The bridging means is adapted for rapid manual removal by an operator.

In the illustrative embodiment, the end cap has a lower rim and the hub has an upper rim. The cap overlies the hub so that the rims are adjacent each other. The bridging means comprises a unitary member having an upper portion and a spaced lower portion. The upper portion is adapted for location on the cap above the cap rim and the lower portion is adapted for location on the hub below the hub rim. Means couple the upper portion to the lower portion.

In the illustrative embodiment, the bridging means is formed as a molded, integral, one-piece member and comprises a generally U-shaped member carrying finger-engaging means for rapid removal.

A more detailed explanation of the invention is provided in the following description and claims, and is illustrated in the accompanying drawings.

BRIEF DESCRIPTION OF THE DRAWINGS

FIG. 1 is an exploded view of a spinal needle assembly constructed in accordance with the principles of the present invention;

FIG. 2 is a front view, partially broken for clarity, of a spinal needle constructed in accordance with the principles of the present invention;

FIG. 2A is a fragmentary view showing the top portion thereof, with the cap separated from the hub;

DETAILED DESCRIPTION OF THE ILLUSTRATIVE EMBODIMENT

Figure 3:
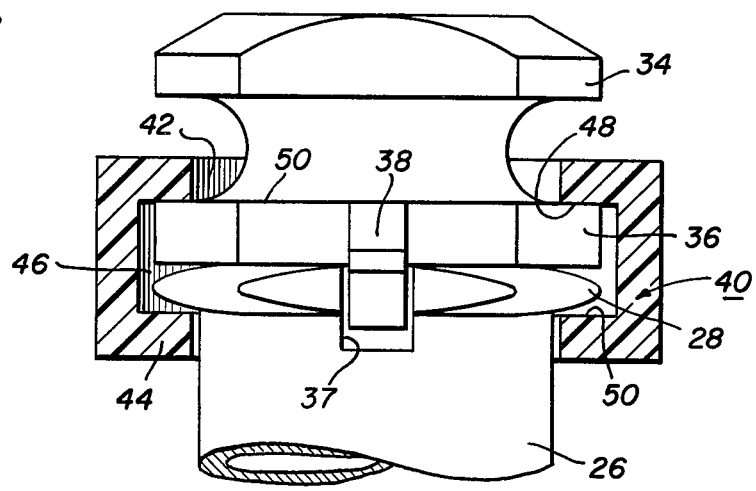
FIG. 3 is an enlarged view, taken partially in cross-section, of the top portion of FIG. 2.

Referring to the drawings, a spinal needle assembly 10 is shown therein, in which a lower housing 12 and a cooperating upper housing 14 removably encase a spinal needle 16.

Spinal needle 16 includes a cannula 18 having a needle bevel 20 at one end and a hub 22 at its opposite end. Hub 22 has a main holding portion 24 and an upper portion 26 carrying an upper rim 28, with the hub defining an axial bore from its top to the needle bevel.

Inserted within the axial bore of cannula 18 and its hub 22 is an obturator 30 comprising a stylet 32 having an obturator cap 34 connected to an end thereof. The obturator cap includes a lower rim 36 which abuts upper rim 28 of upper hub portion 26.

The upper rim 28 defines a slot 37 which cooperates with a cap dink 38 for aligning cap 36 properly with hub 22. When cap 34 and hub 22 are properly aligned, the stylet 32 will be properly located with respect to needle bevel 20. However, in certain prior art constructions if the spinal needle assembly were tilted or tipped, the cap 34 and hub 22 would become improperly aligned, as illustrated in FIG. 2A, thereby moving stylet 32 axially with respect to the cannula. To prevent this possible axial movement, a bridging member 40 is provided for bridging end cap 34 and hub 22 to prevent relative axial movement between the obturator and the cannula.

Figure 4:
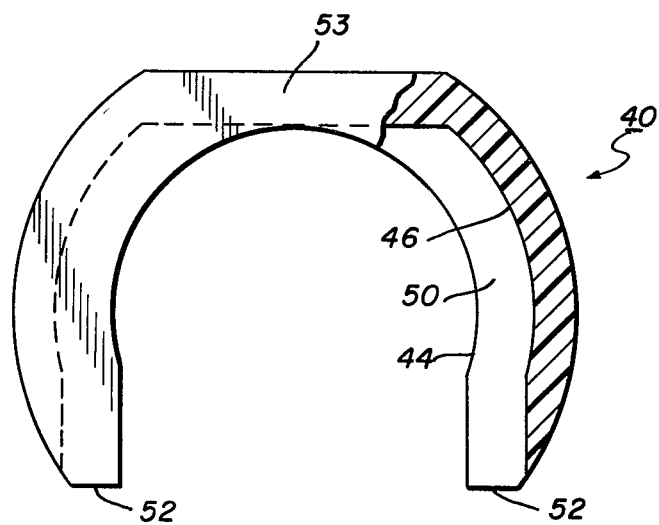
FIG. 4 is a top view, with a portion broken for clarity, of a bridging member used in accordance with the invention.
Figure 5:
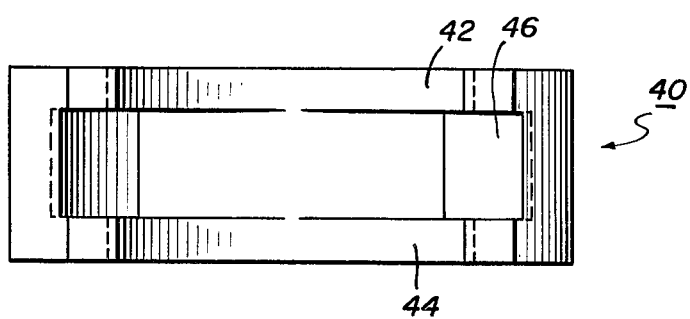
FIG. 5 is an elevational view thereof.
Figure 6:
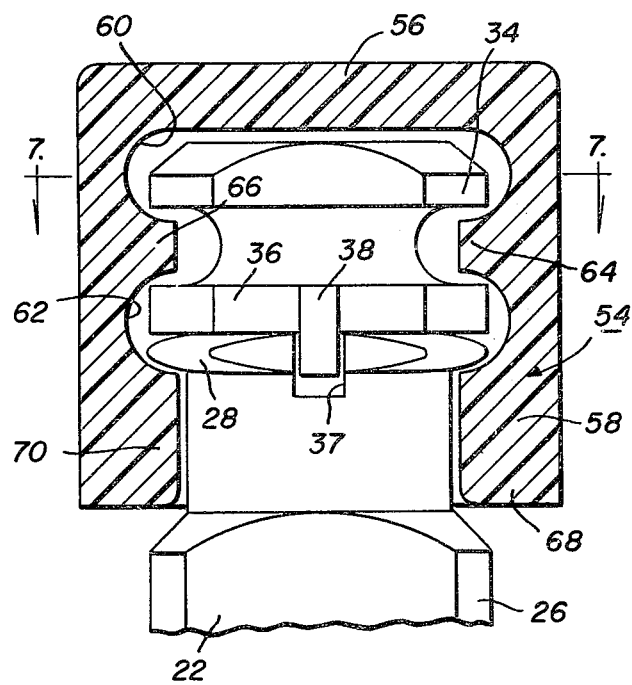
FIG. 6 is an enlarged view of the top portion of a spinal needle, illustrating a modified bridging means which could be used in accordance with the principles of the present invention.
Figure 7:
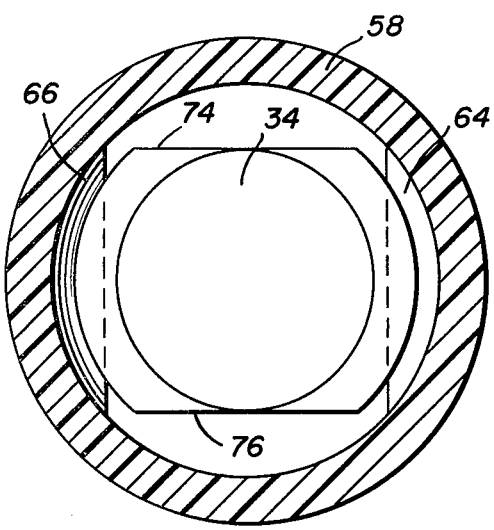
FIG. 7 is a cross-sectional view thereof, taken along the plane of the line 7—7 of FIG. 6.

Bridging member 40 is shown in detail in FIGS. 3-5. The bridging member has a generally U-shaped top configuration and includes an upper portion 42 and a spaced lower portion 44, with portions 42 and 44 being coupled by wall 46. As shown most clearly in FIG. 3. upper portion 42 has a lower surface 48 which engages the upper surface 50 of lower rim 36, and lower portion 44 has an upper surface 50 which engages the underside of upper rim 28, thereby effectively clamping lower rim 36 to upper rim 28. In effect, bridging member 40 acts as a clamp to maintain the cap and hub in proper alignment.

A flattened, front surface 52 of bridging member 40 is provided, so as to enable an operator to manually remove bridging member 40 by simply placing the thumb or thumbnail against surface 52 and pivoting the bridging member away from its connected position. Bridging member 40 is preferably symmetrical so that the flattened, front surface 52 can be provided on both sides to enable easy removal by both right-handed and left handed operators.

Another manner of enabling removal of the bridging member 40 could be gained through the use of a grooved wall section at the bight 53 of the U which would act as a hinge. In addition, a raised section could be provided on the external surface of one or both of the arms of the U to provide a pushing surface for removal.

It is preferred that bridging member 40 be formed of a thermoplastic material which is molded in a unitary, one-piece, integral construction.

Figure 8:
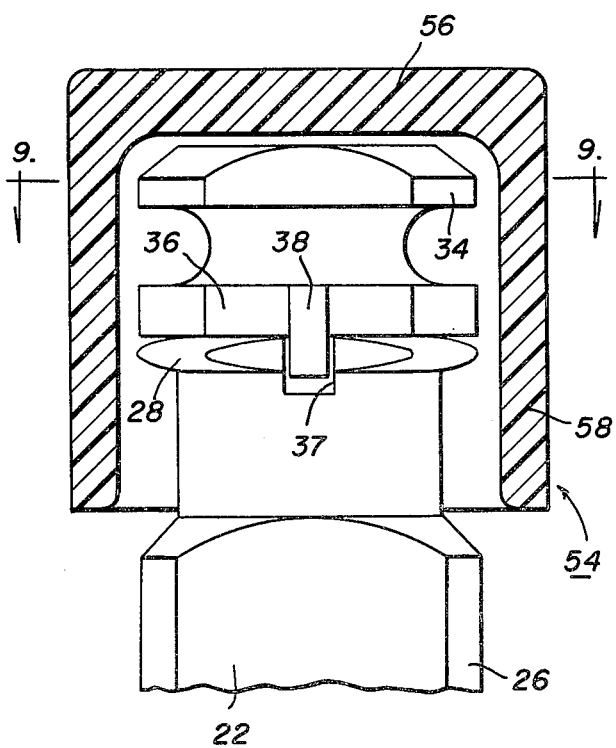
FIG. 8 is a view similar to the view of FIG. 6 but with the bridging means twisted 90°.
Figure 9:
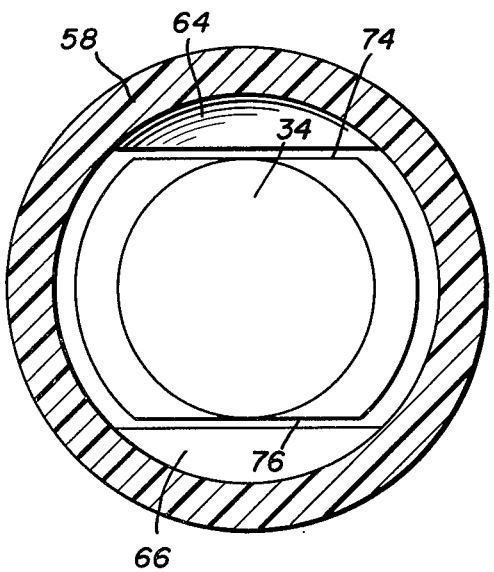
FIG. 9 is a cross-sectional view thereof, taken along the plane of the line 9—9 of FIG. 8.

A modified bridging member 54 is illustrated in FIGS. 6-9. Referring to these figures, bridging member 54 comprises a cap-like member having a top portion 56 and circumferential downwardly depending sidewall 58. In the position illustrated in FIG. 6, the bridging member defines upper groove 60 and lower groove 62 which are formed by inwardly extending members 64 and 66 and also by inwardly extending members 68 and 70. Inwardly extending members 64 and 66 overlie lower rim 36 of cap 34 and members 68 and 70 underlie upper rim 28 of hub 22, to thereby create a clamp with respect to lower rim 36 and upper rim 28. As shown most clearly in FIG. 7, members 64 and 66 (and likewise, members 68 and 70—not shown) are only segmental so that when bridging member 54 is turned 90°, as illustrated in FIGS. 8 and 9, these members will bypass the hub and cap which have flattened sides 74, 76. Thus removal of the bridging member 54 is simplified and merely requires a 90° twist by the opertor.

It can be seen that simplified means have been provided for maintaining the obturator within the lumen of its mated cannula. Further, the operator has the ability to remove the obturator quickly and smoothly once insertion of the spinal needle has been effected.

Although illustrative embodiments of the invention have been shown and described, it is to be understood that various modifications and substitutions may be made by those skilled in the art without departing from the novel spirit and scope of the present invention.

What is claimed is:

1. A spinal needle assembly in which an obturator having an end cap extends into a cannula having a needle bevel at one end and a hub at the opposite end for engagement with said end cap, and means for aligning the obturator and the cannula, the improvement comprising means for bridging said end cap and hub to prevent relative axial movement between said obturator and cannula, said bridging means being adapted for rapid manual removal by an operator and comprising a molded overcap which overlies said end cap and extends over protruding portions of said end cap and hub.

2. An assembly as described in claim 1, said end cap having a lower rim and said hub having an upper rim with said cap overlying said hub so that said rims are adjacent each other, said bridging means comprising a unitary member having an upper portion and a spaced lower portion, said upper portion being adapted for location on said cap above said cap rim and said lower portion being adapted for location on said hub below said hub rim and means coupling said upper portion to said lower portion.

3. An assembly as described in claim 2, said bridging means being formed as a molded, integral, one-piece member.

4. An assembly as described in claim 2, said bridging means further comprising finger-engaging means for rapid removal of the unitary member from the cap and hub.

5. An assembly as described in claim 2, said bridging means being dimensioned so as to prevent its connection to the cap and hub unless the obturator and cannula are properly aligned.

* * * * *